United States Patent [19]

Dorfman et al.

[11] Patent Number: 5,786,068
[45] Date of Patent: Jul. 28, 1998

[54] ELECTRICALLY TUNABLE COATINGS

[75] Inventors: Veniamin F. Dorfman, Stony Brook; Arvind Goel, Buffalo, both of N.Y.

[73] Assignee: Advanced Refractory Technologies, Inc., Buffalo, N.Y.

[21] Appl. No.: 483,848

[22] Filed: Jun. 7, 1995

Related U.S. Application Data

[60] Continuation-in-part of Ser. No. 471,401, Jun. 6, 1995, which is a division of Ser. No. 249,167, May 25, 1994, Pat. No. 5,466,431, which is a division of Ser. No. 695,552, May 3, 1991, Pat. No. 5,352,493.

[51] Int. Cl.$^6$ ............................................. B32B 9/00
[52] U.S. Cl. .................. 428/209; 428/210; 428/408; 428/689; 428/698; 428/701; 428/702
[58] Field of Search ................. 361/502; 428/209, 428/210, 688, 689, 701, 702, 698, 408

[56] References Cited

U.S. PATENT DOCUMENTS

| | | |
|---|---|---|
| 4,191,735 | 3/1980 | Nelson et al. |
| 4,783,368 | 11/1988 | Yamamoto et al. |
| 4,816,291 | 3/1989 | Desphandey et al. |
| 4,822,466 | 4/1989 | Rabalais et al. |
| 4,842,937 | 6/1989 | Meyer et al. |
| 4,877,677 | 10/1989 | Hirocki et al. |
| 4,897,829 | 1/1990 | Ikoma et al. |
| 4,915,977 | 4/1990 | Okamoto et al. |
| 4,948,388 | 8/1990 | Ringwood. |
| 4,960,643 | 10/1990 | Lemelson. |
| 4,961,958 | 10/1990 | Desphandey et al. |
| 4,980,021 | 12/1990 | Kitamura et al. |
| 4,985,051 | 1/1991 | Ringwood. |
| 4,992,298 | 2/1991 | Deutchman et al. |
| 5,002,899 | 3/1991 | Geis et al. |
| 5,040,501 | 8/1991 | Lemelson. |
| 5,055,318 | 10/1991 | Deutchman et al. |
| 5,064,801 | 11/1991 | Juntgen et al. |
| 5,068,148 | 11/1991 | Nakahara et al. |
| 5,077,103 | 12/1991 | Wagner et al. |
| 5,087,434 | 2/1992 | Frenklach et al. |
| 5,094,915 | 3/1992 | Subramaniam. |
| 5,100,424 | 3/1992 | Jang et al. |
| 5,101,288 | 3/1992 | Ohta et al. |

(List continued on next page.)

FOREIGN PATENT DOCUMENTS 2 158 086 3/1985 United Kingdom.

OTHER PUBLICATIONS

Dorfman, "Diamond–Like Nanocomposites (DLN)", Thin Solid Films, 267–273:212 (1992).

R. d'Agostino, ed., "Plasma Deposition, Treatment and Etching of Polymers", Academic Press, San Diego, 1990.

Dorfman, V.F., et al., Sov. Phys. Dokl., 28 (1983) 743 (English Abstract).

Dorfman, V., "Synthetics of Solid State Structure", Metallurgia, Moscow (1986).

Dorfman, V., et al. Diamond Films '90, Proc. 1st European Conf. on Diamond and Diamond–Like Carbon Coatings, Crans–Montana (1990).

Weissmantel et al. J. Vac. Sci. Technol. vol. A4, 2892.

Dorfman, et al. J. Tech. Phys. Lett., 14:1033 (1988).

Ageev, "Lighted Induced Variations of Optical Properties of Diamond–Like Films", Surface and Coating Technologies, 47:269–278 (1991).

*Primary Examiner*—Patrick Ryan
*Assistant Examiner*—Elizabeth Evans
*Attorney, Agent, or Firm*—Nixon, Hargrave, Devans & Doyle

[57] ABSTRACT

An electrically tunable coating and method for its fabrication and deposition comprising, as a coating on a substrate, a diamond-like nanocomposite solid-state material having interpenetrating atomic scale networks of carbon in a diamond-like carbon network stabilized by hydrogen, a glass-like silicon network stabilized by oxygen, and optionally at least one additional network of dopant elements or dopant compounds having elements from groups 1–7b and 8 of the periodic table.

29 Claims, 6 Drawing Sheets

U.S. PATENT DOCUMENTS

| | | |
|---|---|---|
| 5,110,577 | 5/1992 | Tamor et al. . |
| 5,135,808 | 8/1992 | Kimock et al. . |
| 5,137,784 | 8/1992 | Suzuki et al. . |
| 5,142,390 | 8/1992 | Ohta et al. . |
| 5,158,828 | 10/1992 | Sudani et al. . |
| 5,169,579 | 12/1992 | Marcus et al. . |
| 5,171,732 | 12/1992 | Hed . |
| 5,174,983 | 12/1992 | Snail . |
| 5,177,299 | 1/1993 | Kondo et al. . |
| 5,183,602 | 2/1993 | Raj et al. . |
| 5,190,807 | 3/1993 | Kimock et al. . |
| 5,198,285 | 3/1993 | Arai et al. . |
| 5,202,571 | 4/1993 | Hirabayashi et al. . |
| 5,206,083 | 4/1993 | Raj et al. . |
| 5,210,430 | 5/1993 | Taniguchi et al. . |
| 5,219,769 | 6/1993 | Yonehara et al. . |
| 5,243,199 | 9/1993 | Shiomi et al. . |
| 5,256,483 | 10/1993 | Yamazaki et al. . |
| 5,352,493 | 10/1994 | Dorfman et al. . |
| 5,383,089 | 1/1995 | Williams .................. 361/502 |

ELECTRICALLY TUNABLE COATINGS

This application is a continuation-in-part of U.S. patent application Ser. No. 08/471,401, now pending, filed Jun. 6, 1995 as a divisional of U.S. patent application Ser. No. 08/249,167, filed May 25, 1994 (now issued as U.S. Pat. No. 5,466,431), which is a divisional of U.S. patent application Ser. No. 07/695,552, filed May 3, 1991 (now issued as U.S. Pat. No. 5,352,493).

This invention was developed with government funding under Department of Defense Contract No. F29601-93-C-0160. The U.S. Government may have certain rights.

BACKGROUND OF THE INVENTION

Field of the Invention

The present invention relates to electrically tunable coatings for substrates.

The use of diamond-like coatings and chemical vapor-deposited diamond film technologies is known. While diamond-like coatings (DLCs) are known to be superior coatings for many substrates, their use as coatings for substrates subjected to high temperatures and electrical currents has led to practical problems.

Many of the DLC coatings available in the field often display superior thermal characteristics, but have been susceptible to ablation, or long-term adherence problems. No known DLC material adequately imparts all of the necessary characteristics to substrate materials used as dielectrics; for example, insulators in electronics, and especially devices used in plasma-related devices.

DLCs often have-adherence problems which require depositing additional interlayers between the DLC and the substrate. In addition, intrinsic stresses limit the allowable deposition thickness of the DLC. While thicker DLCs may be desirable to protect the substrate, delamination of the DLC from the interlayer and the substrate will result if the DLC is deposited onto the substrate to form an overly thick DLC layer.

In certain dielectric applications, no current leakage is desirable. In this circumstance, the dielectric coating selected must inhibit dielectric "breakdown" whereby current passes through the coating to, or even through, the substrate. Further, in many applications, the material used as the dielectric coating must also inhibit "flashover" whereby some of the charge at one conductive point on the coating surface passes over the surface to another conductive point, eroding the surface between and around the conductive points. Further, in some applications, it may be desirable for the coating to have at least some ability to conduct and direct charges away from the surface to keep the charge from building up and having "flashover" or "breakdown" occur.

Known DLCs may perform well initially as dielectric coatings. However, over time, exposure to high currents leads to the graphitization of the carbon in the DLC network. Upon graphitization, the DLCs becomes more conductive, thereby frustrating the purpose for the coating as a dielectric material and rendering the substrate useless, or at least more conductive than is desired.

The lack of an adequately coated and insulated electrical component often results in the failure or shorter lifetime of the device served by the component. Further, radiation effects, including ultraviolet radiation and ion-bombardment often accelerate DLC deterioration through erosion or graphitization of the DLC coating.

SUMMARY OF THE INVENTION

Accordingly, the present invention relates to electrically tunable coatings for use as superior dielectric coatings.

According to one feature, the present invention is directed to a method of inhibiting conductivity on a substrate by applying to said substrate a tunable dielectric coating formed from a diamond-like solid-state material comprising interpenetrating atomic scale networks of a diamond-like carbon network stabilized by hydrogen, a glass-like silicon network stabilized by oxygen, and optionally at least one additional network of dopant elements or dopant compounds having elements from groups 1–7b and 8 of the periodic table.

In another feature, the present invention is directed to a method of selectively modifying the conductivity of a substrate by applying to said substrate a tunable coating made from a diamond-like material having interpenetrating atomic scale networks comprising a first diamond-like carbon network stabilized by hydrogen, a second glass-like silicon network stabilized by oxygen, and optionally at least one network of dopant elements or dopant compounds having elements from groups 1 to 7b and 8 of the periodic table.

In still another feature, the present invention is directed to a tunable coating formed from a diamond-like solid-state material comprising an interpenetrating diamond-like carbon network stabilized by hydrogen, a glass-like silicon network stabilized by oxygen, and optionally at least one network of dopant elements or dopant compounds having elements from groups 1–7b and 8 of the periodic table.

In a still further feature, an electrically tunable coating having a predetermined resistivity is disclosed, said coating being made from a class of diamond-like solid state materials formed from interpenetrating networks, said networks comprising a first diamond-like carbon network stabilized by hydrogen, a second silicon network stabilized by oxygen and, optionally, at least one network of dopant elements, or compounds having elements from groups 1–7b and 8 of the periodic table.

In another feature, the present invention is directed to an electrically tunable material with a selectively modified resistivity made from a substrate and a tunable coating on the substrate, said coating made from a class of diamond-like solid state materials formed from interpenetrating networks, said networks comprising a first network of carbon in a diamond-like carbon network stabilized by hydrogen, a second silicon network stabilized by oxygen and, optionally, at least one network of dopant elements, or compounds having elements from groups 1–7b and 8 of the periodic table.

DETAILED DESCRIPTION OF THE INVENTION

The present invention relates to a method of selectively modifying conductivity on a substrate by applying to said substrate an electrically tunable coating made from a diamond-like solid-state material having interpenetrating atomic scale networks of carbon in a diamond-like carbon network stabilized by hydrogen, a glass-like silicon network stabilized by oxygen, and optionally at least one additional network of dopant elements or dopant compounds having elements from groups 1–7b and 8 of the periodic table.

The fundamental structure of the preferred tunable dielectric coatings of the present invention are atomic scale diamond-like nanocomposites (DLNs). The DLNs are comprised of two or more self-stabilized random networks. Each network is itself stabilized chemically, while both networks also structurally stabilize each other. An example of a material with such a structure is the diamond-like nanocomposite (DLN) which is the subject of U.S. Pat. No. 5,352,493 and U.S. Ser. No. 08/249,167 filed May 24, 1994. In the DLN, a first random carbon network, mainly in the form of "diamond-like" bonds is chemically stabilized by hydrogen atoms. A second glass-like silicon network is chemically stabilized by oxygen atoms, resulting in a purely amorphous structure. The tunability of the coating may be achieved by varying the content and concentration of the optional additional networks made from dopant elements or dopant compounds. The tunability desired is also achieved by closely controlling the deposition conditions of the coatings.

"Amorphous" as used herein refers to a random structure or arrangement of atoms in a solid state that results in no long range regular ordering, and lacks crystallinity or granularity. Such DLNs contain no clusters or ordering greater than about 10 Angstroms. This absence of clusters at the atomic scale is a key characteristic of the DLN coatings of the present invention. Clusters can destroy the amorphous nature of the structure, and can serve as active centers of degradation.

This structure has been confirmed via electron projection methods, scanning tunneling microscopy, atomic force microscopy, glancing x-ray and electron diffraction techniques and high resolution transmission electron microscopy (TEM). Cluster formation is prevented in the sources, in the primary plasma, in the chamber space, and during film growth.

Figure 1A:
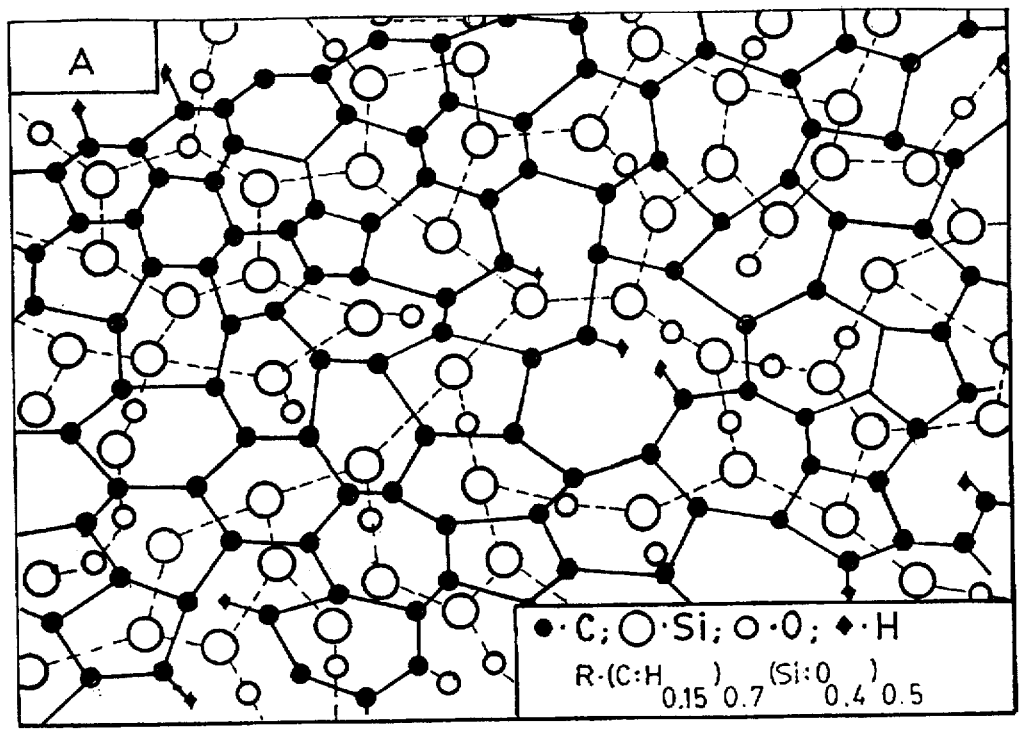
FIG. 1 is a schematic diagram showing the principle microstructure of two-network (A), intermediate (B), and three-network (C) nanocomposites.
Figure 1B:
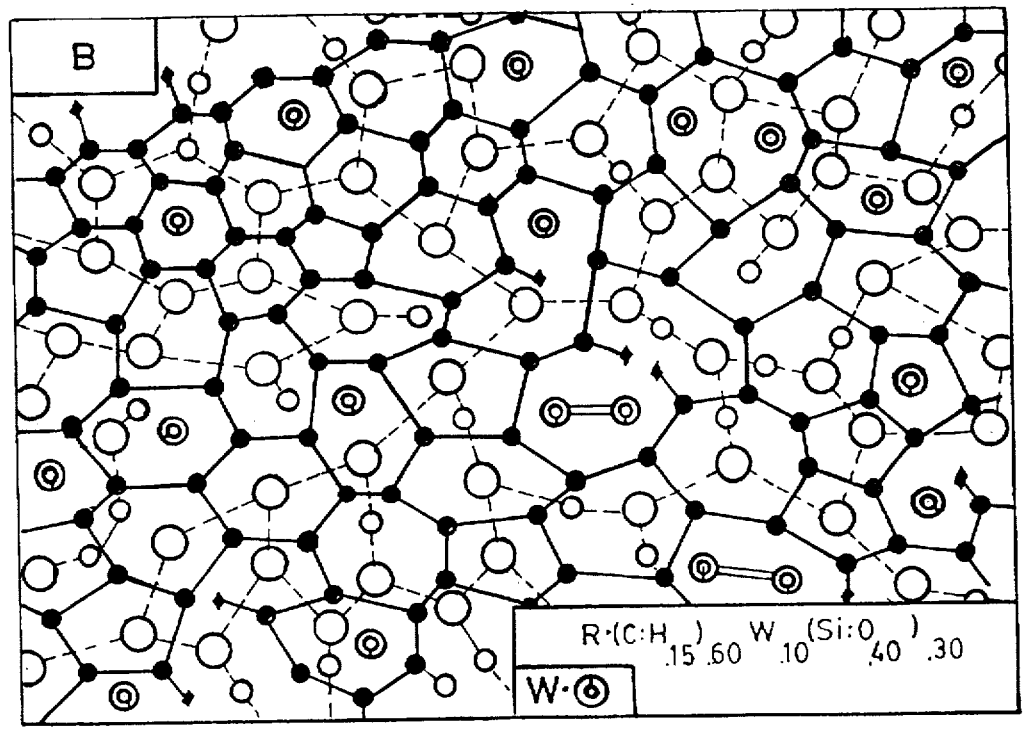
Figure 1C:
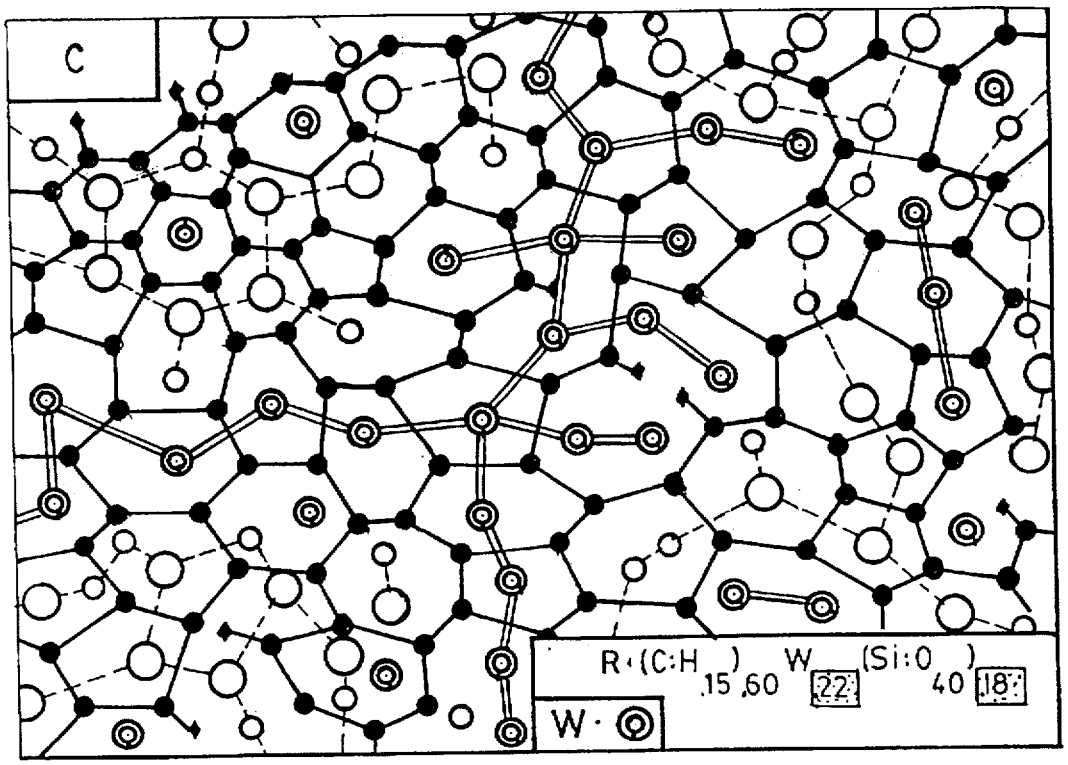

The atomic structure of the class of diamond-like nanocomposite (DLN) solid state materials of the present invention is shown in FIG. 1(A). The DLNs may have one or more additional separate disordered networks of dopants, as shown in FIGS. 1(B) and 1(C). The dopants may be any one, or a combination of transition metals and non-metals of the groups 1b–7b and 8 of the periodic table, with all three types of networks (C—H; Si—O and the dopant network, Me-Me) are bonded to each other predominantly by weak chemical bonds. The network elements other than the C—H network may also be referred to as alloying elements. Silicon and oxygen may also be used in dopant networks with other dopant elements or dopant compounds.

When the optional, additional dopant-containing network is present, the dopant network is interspersed along with the previously mentioned two interpenetrating networks. In this instance three or more interpenetrating networks will be present in the DLN to form a so-called Me-DLN (metal-diamond-like nanocomposite) network. It is understood that non-metal dopant networks, may be incorporated as the optionally present dopant networks interpenetrating the C—H and Si—O networks. It is further understood that when dielectric coatings are desired, non-conductive dopants may be incorporated as the third network. This may include conductive elements which are reacted to yield a non-conductive compound. When tunably conductive coatings are desired, conductive elements and compounds may be used as the dopants in the dopant network.

The three networks (C—H matrix, Si—O matrix and a dopant matrix) are bonded to one another mainly by weak chemical attractive forces. Carbide formation can be prevented even at metal concentrations as high as 50% (verified using Auger electron spectroscopy, electron spectroscopy for chemical analysis (ESCA), extended x-ray absorption fine structure spectroscopy (EXAFS) and Fourier transform infrared spectroscopy (FTIR) can be achieved. Again, the properties of these materials can be varied over wide ranges depending on the dopant and the concentration selected, as well as the deposition technique and parameters. As already mentioned, the structure of these composites can be tailored at the molecular level. Therefore, unique electrical, optical, and other desirable solid state properties with desired mechanical strength, hardness and chemical resistance can be imparted on the DLN coatings.

Preferred dopant elements to be used in the Me-DLN network, and which are particularly effective for use as dopants in a tunable dielectric Me-DLN coating are B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag and Au; with W, Cr, Zr, Ti and Hf being most preferred. Preferred compounds which may be used as dopants include TiN, BN, AlN, ZrN and CrN with TiN, AlN and CrN being most preferred.

The carbon content in the diamond-like nanocomposite is greater than about 40 atomic % of the DLN. Although the DLN may theoretically be prepared without any hydrogen, the hydrogen content is preferably at least about 1 atomic % and up to about 40 atomic % of the carbon concentration. The sum of the silicon, oxygen and dopant elements and dopant containing compounds is greater than about 2 atomic % of the DLN. In one preferred embodiment, the ratio of carbon to silicon atoms is from from about 2:1 to about 8:1, hydrogen to carbon atoms is about 0.01:1 to about 0.4:1, silicon to oxygen atoms is about 0.5:1 to about 3:1, and dopant to carbon atoms is about 0:1 to about 1.5:1. Therefore, in the DLN network, for every 1 part carbon, there is from about 0.01 to about 0.4 parts hydrogen, from about 0.125 to about 0.5 parts silicon, and from about 0.0375 to about 1.0 parts oxygen. In such a scheme, if a third dopant network were present, for every 1 part carbon, there would be from about 0.01 to about 1.5 parts dopants depending upon the desired characteristics to be imparted to the Me-DLN network.

The conductive properties of these DLN materials can be varied over wide ranges from a dielectric coating to a highly conductive coating, depending on the dopants and concentrations selected, as well as the deposition conditions. As already discussed, the structure of these composites can be tailored or "tuned" at the molecular level to combine unique electrical, optical, and other desirable solid state properties with "tunable" mechanical strength, hardness and chemical resistance properties. It is important that the coatings of the present invention be hard, resilient and able to withstand wear and friction normally associated with use as an electrical component.

It is contemplated that single layers or multiple layers of the identical or differing (based on chemical content) doped and undoped DLNs may be used to give the desired resistivity and other physical properties. Such multilayered coatings would be useful for making ultracapacitors capable of very high capacitance. Such ultracapacitors may be about 10 nm thick and be comprised of 100 or more doped and undoped layers.

The electrical properties of the DLN structures of this class of materials can be continuously varied over at least 18 orders of magnitude from a purely dielectric material, at about $10^{-5}$ Ohm·cm, to a metallic state, at about $10^{15}$ Ohm·cm, while preserving the properties of the DLN state. A transition to a superconducting state, with the absence of electrical resistivity, is observed at low temperatures for certain three-network nanocomposite networks.

When a completely dielectric coating is desired, the two-network DLN may be used. In addition, to impart certain hardness characteristics a three-network DLN may be used; but in this instance non-conductive dopants would be used to ensure the superior performance as a dielectric coating. The good adherence and superior hardness of the DLNs of the present invention make the DLNs good candidates as coatings for devices such as slip rings or any electrical components which routinely are exposed to harsh chemical or physical conditions such as friction. The DLNs greatly reduce wear of the slip rings while maintaining a high amount of constant electrical contact.

A completely dielectric coating would inhibit surface "breakdown" and offer superior substrate protection. The breakdown strength of the DLNs of the present invention ranges from about $10^6$ to about $10^9$ V/cm depending upon the chemical substituents of the DLN coating applied to the substrate.

However, it is often desired that some of the residual charge occurring at the surface near the contacts be conducted away to prevent charge build-up and surface erosion from "flashover". For example, anti-static coatings and other electronic component coatings are used to direct away rather than retain a charge on the surface. The flexibility of the tunable DLN coatings of the present invention is especially advantageous for this purpose. The optional, third dopant network can be tailored to include an appropriate concentration of selected conductive dopant to offer the required amount of conductivity at the surface layer of the DLN coating to avoid "flashover" effects. The flashover resistivity of the DLNs of the present invention ranges from about 59,000 V/mm to about 3000 V/mm depending on the chemical substituents present in the DLN coating applied to the substrate.

To improve adherence, DLC coatings often place an intermediate layer between the substrate and the DLC coating. However, this intermediate layer limits the useful thickness of the DLC coatings. If the DLC coatings are too thick, delamination occurs.

Surprisingly, with the DLN coatings of the present invention, adherence is so good that an interlayer is not required. As a result, the coating material may be applied more thickly without risking delamination from the substrate. The thicker layer of DLN coating in turn is believed to contribute to the superior erosion resistant properties of the tunable DLN cooatings and tunable DLN-coated substrates.

The presence of the glass-like silicon network, stabilized by oxygen, serves to prevent the growth of graphitic carbon at high temperatures and, to prevent metal cluster formation in metal-containing three-network nanocomposites, as well as reducing the internal stress in the nanocomposite structure, thereby enhancing the DLN adhesion directly to substrates. This appears to lead to superior adherence of the DLNs of the present invention to the substrate material.

To be useful as dielectric coatings, the coatings must have predictable non-conductive or minimal conductive properties which must not vary over time; or in response to extreme conditions, such as heat. Most importantly, the coatings must not degrade into forms of elements which become more conductive. One such element is carbon which, upon transformation through graphitization, becomes more conductive than the original DLC coating.

The DLN coatings of the present invention have temperature stability far exceeding that of traditional diamond-like (DLC) materials. Crystalline diamond is stable to approximately 1100° C., upon which graphitization occurs. Quartz has long term thermal stability to 1470° C., and short term thermal stability up to 1700° C. Traditional, non-alloyed diamond-like films are stable only to about 600° C. before graphitization occurs. Alloyed DLC films are much less thermally stable.

By contrast, the DLN structure used to provide the tunable dielectric coatings of the present invention has long term stability to 1250° C. and short term stability to 2000° C.; i.e. thermal stability of the DLN exceeds that of crystalline diamond while preserving the amorphous, diamond-like state.

In the range of from about 600° C. to about 1000° C., the chemical bonds of the carbon matrix of DLN materials partly change from $sp^3$ to $sp^2$. However, the general structure of the nanocomposite and their "diamond-like" properties are preserved. By contrast, under similar conditions, the usual "diamond-like" carbon (DLC)is graphitized and loses its diamond-like properties. Further, in the range of from 400° C. to 500° C. (preferably 430° C.), a reverse annealing is observed, whereby the ratio of $sp^3$ to $sp^2$ is increased. Inhibiting graphitization of the carbon is critical for preserving dielectric properties, as graphitized carbon is more conductive than the network-protected DLC. Therefore, the ability of the DLN coatings to be more thermally stable than the DLCs gives the tunable dielectric DLN coatings a significant advantage over DLC coatings, in terms of inhibiting conductivity.

The density of the C—H and Si—O two network DLN varies from about 1.8 to about 2.1 g/cm³. The rest of the space is taken up by a random network of nanopores with diameters varying from about 0.28 to about 0.35 nm. The nanopore network does not form clusters or micropores. The properties of the two network DLN may then be tailored by adding dopant. The dopants fill the nanopore network in a random fashion, eventually resulting, at a certain dopant concentration, in an additional network without clusters or microcrystalline grains, even at concentrations as high as 50 atomic %. At concentrations below about 10 atomic %, the dopants are distributed as separate atoms in the nanopores of the diamond-like matrix. The average distance between dopant atoms in this quasi-random structure can be controlled by the concentration of the dopant. When the relative concentration of the dopant element or compound reaches about 20–25 atomic %, the dopants form the third (Me-Me) network in the DLN structure as shown in FIG. 1(C), resulting in a material with diamond-like mechanical and chemical properties.

Figure 2:
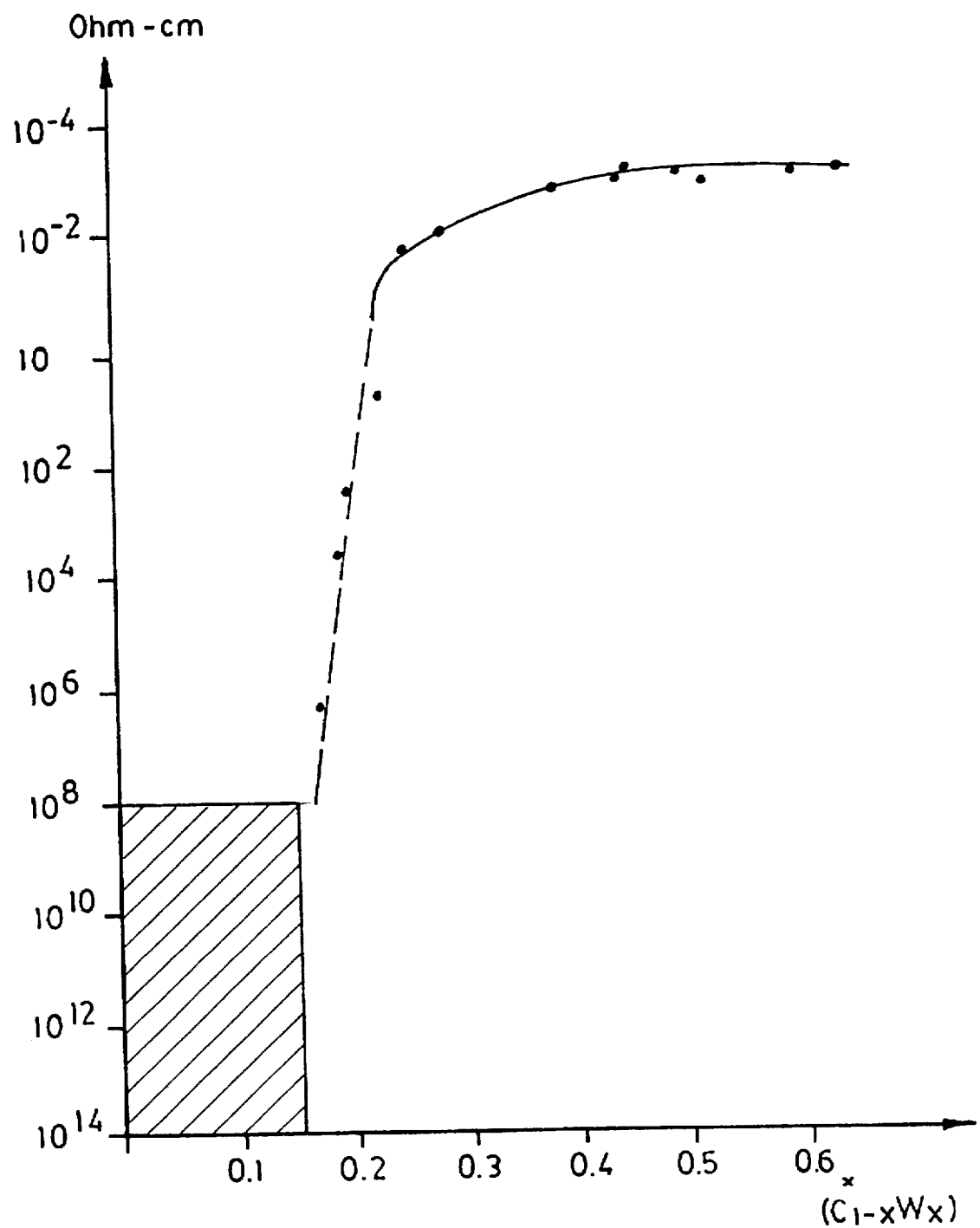
FIG. 2 is a schematic diagram showing the dependence of electrical resistivity on concentration for the case of a W-DLN nanocomposite.

FIG. 2 shows the resistivity in ohm-cm as a function of the concentration of tungsten (W) for a W-alloyed film. Metallic conductivity is reached for a W concentration in the range of from about 15 to about 50 atomic % of the dopant element.

Figure 3:
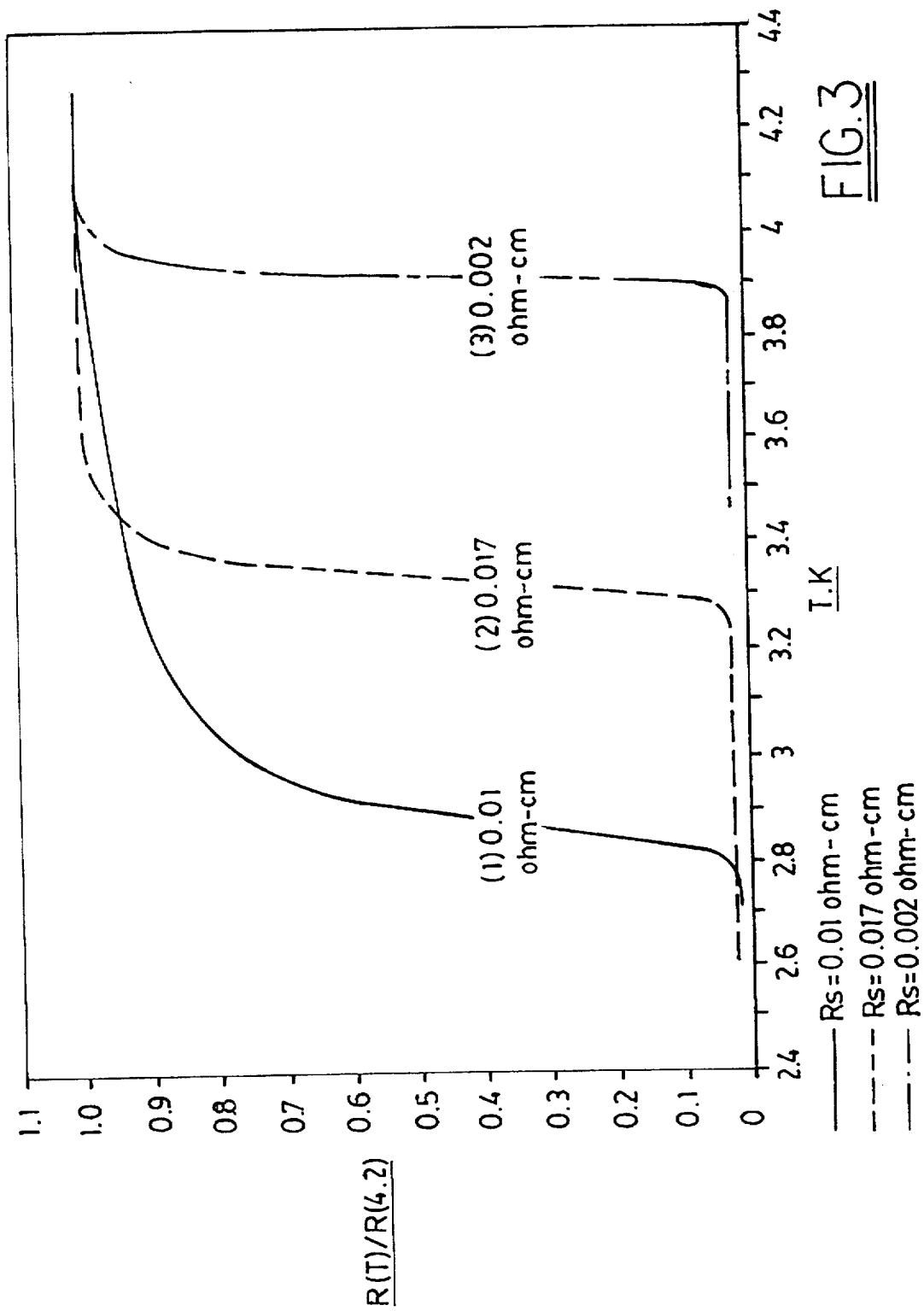
FIG. 3 is a schematic diagram showing the dependence of electrical resistivity on temperature for a W-alloyed film.

FIG. 3 shows the dependence of electrical resistivity on temperature for a tungsten doped DLN film (W-DLN). The graph demonstrtaes the transition to a superconducting state. Curves 1, 2, and 3 correspond to W-DLN films with room temperature resistivities of 0.01, 0.017 and 0.02 Ohm·cm respectively.

In the intermediate concentration range, where the dopant concentration is from about 10 to about 20 atomic %, the dopants form a fragmented, random network, without true network-like connectivity. The electronic properties of the fragmented dopant "network" depend strongly on external mechanical loading, pressure and electromagnetic fields. The Me-DLNs with dopant concentrations in the range of from about 1- to about 20 atomic % are ideal use as smart materials and sensors. "Smart" materials are understood to be materials that not only sense an external stimulus, but also can react and make appropriate adjustments in response.

As already mentioned, the specific dielectric properties of the DLN coatings can be altered or selectively "tuned" by closely monitoring the amount of metal incorporated as the third-network during layer deposition. The three-network coating may also be applied as a layer alternating with two-network DLN coating layers to achieve desired dielectric effects such as capacitance. Further, the dopant type and concentration may be selectively varied, as may be the deposition conditions.

Another advantage of the DLNs of the present invention is their relative hardness and durability. The DLNs, especially the metal doped DLNs combine high microhardness with high elasticity. The microhardness values of the DLNs of the present invention range from about 6 to about 30 GPa.

The DLNs may be synthesized via co-deposition by clusterless beams of ions, atoms or radicals of the relevant elements, where the mean free path of each particle species exceeds the distance between its source and the growing particle film surface, and each beam contains particles of well-defined energy. Carbon-containing particle beams can be produced by plasma discharge in a plasmatron and extracted as charged particles by a high-voltage field in a vacuum chamber and directed onto the substrate.

At least 50% of the carbon-containing particles have kinetic energy above about 100 eV. The temperature of the substrate during growth should not exceed 500° C.

Figure 6:
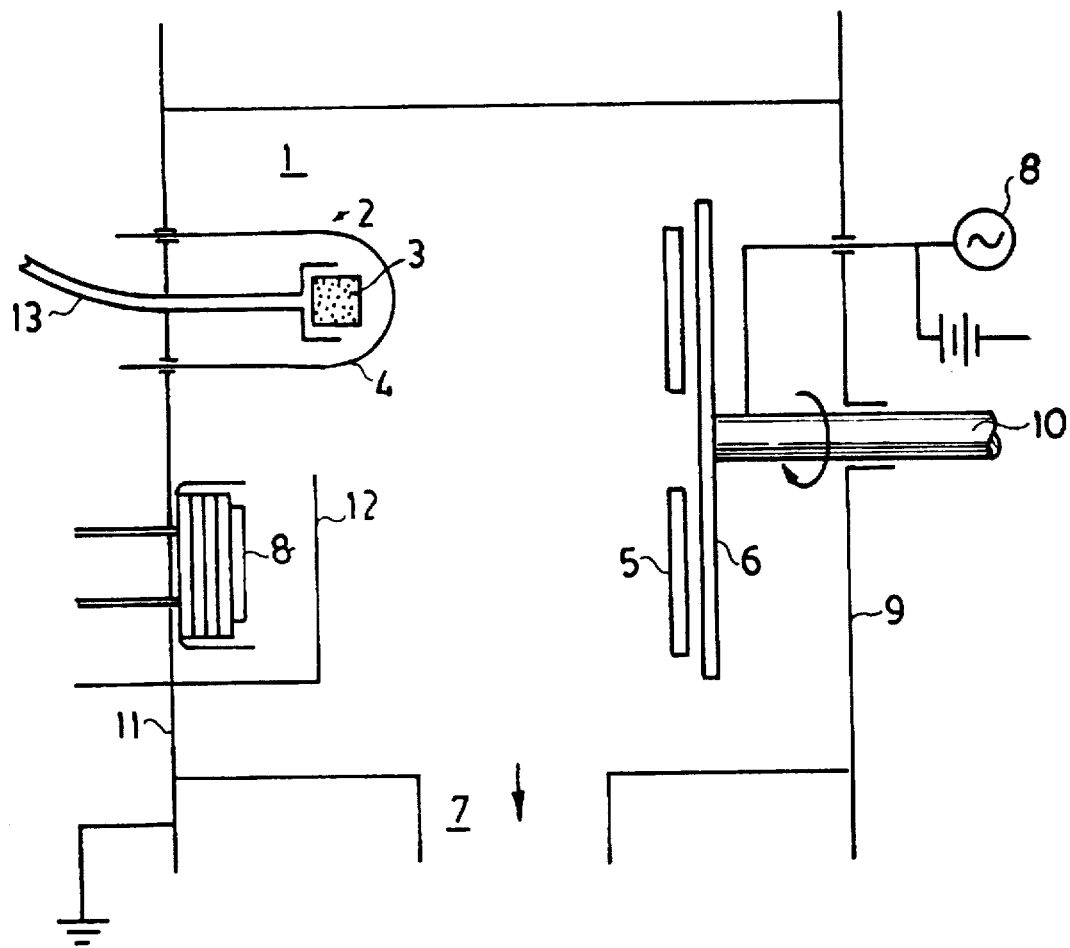
FIG. 6 is a cross section view of a preferred deposition chamber using a plasma source integrally located within the chamber.

FIG. 6 shows one preferred embodiment of the coating chamber used for the DLN coating deposition process. A vacuum deposition chamber 1 is provided to coat a substrate sample. A precursor inlet system 13, comprises a metal tube and a porous ceramic material 3 through which a liquid precursor, preferably a polysiloxane, is injected. The precursor inlet system 13 is shown incorporated into the chamber through the chamber base plate 11. The thermocathode 2 comprises a resistively heated thoriated tungsten filament 4. Substrates 5 to be coated with DLN film are attached to the substrate holder 6. The power supply 8 is used for biasing the substrates (DC or RF). In practice the system is "pumped down" using normal vacuum pump down procedures. A gate valve (not shown) located on port 7 is closed and the system is backfilled with dry air, nitrogen or argon until the chamber reaches atmospheric pressure. The door of the chamber, 9, is then opened and substrate to be coated 5 are attached to the substrate holder 6 using any of many possible methods (spring clip, screw, clamp, etc.). Special fixtures may be required for substrates of special shapes. The substrate holder is designed in a way that it will also hold a cylinder sample (not shown), which, in operation, rotates both about the axis of the central drive shaft 10, and its own axis which is perpendicular to 10. In this way, the axis of the cylinder would be perpendicular to the axis of 10.

When the substrates are loaded, the door of the chamber is closed, the chamber evacuated and the gate valve opened to bring system pressure down to at least $10^{-5}$ to $10^{-6}$ Torr, which is the desired range of system base pressure. When the above base pressure is achieved, argon gas is introduced into the chamber via a needle valve or mass flow controller, until the chamber pressure reaches approximately $5 \times 10^{-5}$ to $1 \times 10^{-3}$ Torr, preferably about $1-3 \times 10^{-4}$ Torr. At this point the filament current, the filament bias and the electromagnet power supply are switched on. The filament current is the current that passes through the thermocathode (also called the filament or the cathode). The filament bias is the constant floating voltage applied to the filament (approximately $-150$V in relation to ground). Plasma current is measured as the current between the filament and the base plate or ground. This voltage provides the field that moves electrons emitted by the filament to the base plate 11. The electromagnet power supply provides current to the electromagnet, which creates a magnetic field that results in the electron path becoming a spiral, increasing the electron path length and improving the probability of collisions between the electrons and the vapor molecules created due to precursor evaporation. The substrate bias power supply is concurrently switched on.

Switching on these power supplies results in creation of an argon plasma, which is used to clean the substrates prior to deposition. After the required duration of cleaning, the precursor supply is opened. Precursor flow is controlled via a needle valve and occurs due to the difference in pressure between the chamber and the outside atmosphere. When precursor flow and vaporization in the chamber has stabilized, the argon gas flow is turned off. The ionized precursor vapors form a stable plasma, ions from which are accelerated towards the substrate holder due to the substrate bias. Thus, deposition of DLN film occurs.

Co-deposition of a dopant material is carried out as follows. Argon flow to the magnetron is commenced and the magnetron 8 is switched on after the base pressure has been reached. A shutter 12 is used to prevent deposition while the substrate is cleaned via sputtering. When cleaning has been accomplished, the shutter 12 is opened and sputtering is carried out at the desired power level. This may occur prior to commencement of DLN film deposition, during DLN film deposition, after DLN film deposition, or intermittently during DLN film deposition, depending on what kind of film structure and composition are desired. Using DC or RF sputtering, materials of all kinds (metals, ceramics, alloys, etc.) can be used for co-deposition.

Figure 4:
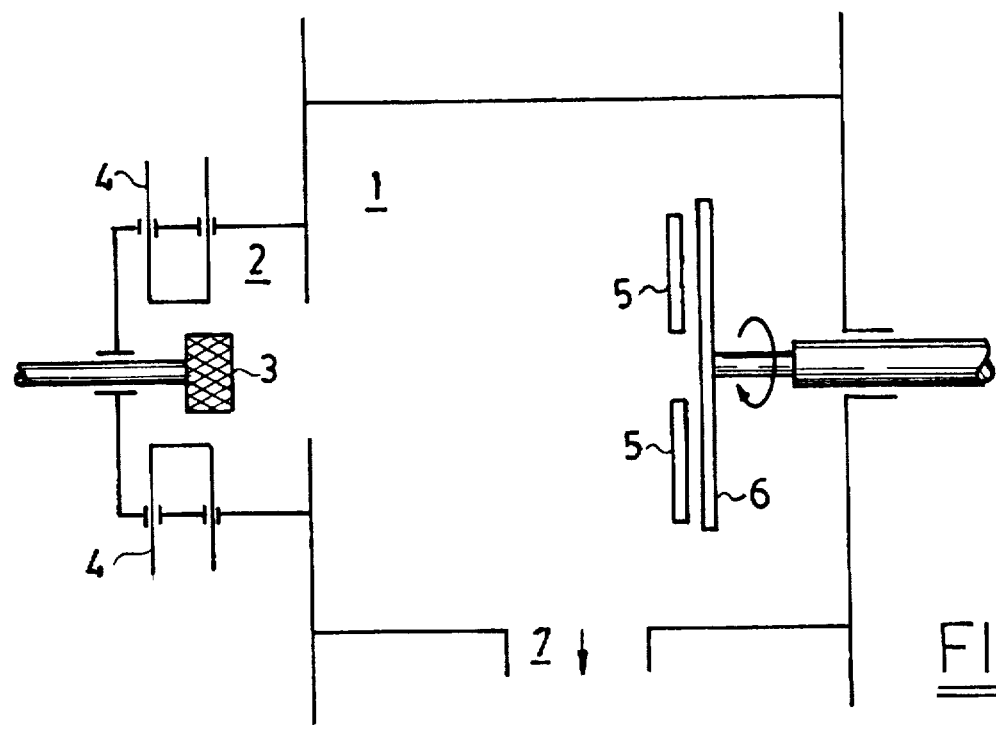
FIG. 4 is a cross section view of the deposition chamber for the deposition of the DLNs.

The growth conditions for nanocomposite films are the following, with reference to FIG. 4. The pressure in the deposition chamber 1 should not exceed $10^{-3}$ torr, with the pressure in the active zone of the plasma generation 2, in the range from about $1.0 \times 10^{-3}$ to about $5.0 \times 10^{-2}$ torr. The temperature of the substrate should not exceed about 200° C. with the temperature of the cathode filaments being in the range from about 2100° to about 2950° C. The current in the cathode filament is from about 70 to about 130 A, with the voltage across the filament being from about 20 to about 30 V. The voltage with respect to the ground is from about 70 to about 130 V with the plasma current being from about 0.5 to about 20.0 A. The voltage of the substrate holder is from about 0.1 to about 5.0 Kv, with all the carbon-containing and Si-containing species having kinetic energy in the range of from about 100 to about 1200 eV and from about 25 to about 300 eV respectively. The metal beams consist of free atoms or monatomic ions. The kinetic energy of the metal atoms/ions does not exceed from about 25 eV. With a precursor flow rate from about 0.5 to about 5.0 cc/hour, the growth rate of the DLN is from about 0.1 to about 2.0 micrometers/hour.

The preferred range of operation for most applications is a pressure of about $1-3 \times 10^{-5}$ Torr, a plasma current of about 1 amp., a filament current of from about 60 to about 75 amp., a substrate voltage of from about 600 to about 1000 V DC, or forward power of about 100 W in RF mode. The preferred frequency for RF mode is from about 90 to about 300 KHz. The preferred magnetron power depends on the type of material, composition and structure desired for the DLN coating.

In a further preferred embodiment, a preferred method of deposition uses a plasma discharge in a triode plasmatron, as shown schematically in FIG. 4, with the plasma energy density above about 5 Kwh/gram-atom of carbon. The charged particles are extracted by a high voltage field in the vacuum chamber and directed onto the substrate. It is preferable that the potential of the substrate holder is from about −0.3 to about +5.0 Kv, and most preferably 1.0+/−0.2 Kv, and varying with a frequency in the range of from about 0 to about 25 Mhz for DC and from about 90 to about 300 KHz for RF. The ratio of the electron emission to the carbon precursor flow in the plasmatron is from about 0.5 to about 1.5 electrons per particle.

Organosilicon compounds, such as siloxane, are preferred precursors for C, H, Si and O. One preferred organosilicon compound is polyphenylmethylsiloxane, containing 1 to 10 Si atoms. The high boiling point siloxanes may be introduced directly into the active plasma region through a porous ceramic or metallo-ceramic (3 in FIG. 4 and FIG. 5) which is heated via radiation thermocathodes 4. The photon and electron emission of the thermocathodes affect the evaporation, fragmentation and ionization of the precursor molecules on the surface of the ceramic, which thereby functions as an ion source for the plasma generator. An alternative method for injection of the siloxane precursors is to use direct injection from a diffusion pump.

The formation of dopant-containing beams may be realized by any one of, or combination of, the following methods: 1) thermal evaporation; 2) ion-sputtering; 3) ion beams. The dopant-containing beams are directed onto the growing film surface through the vacuum chamber to exclude interparticle collisions in the deposition chamber itself. Substrates are placed in an adjacent chamber on a rotating substrate holder, (for example a drum) which ensures double rotary motion, said adjacent chamber being connected to the plasma generation chamber by an opening for the emission of the atomic or ionic beams, as shown schematically in FIG. 4. Alternatively, the plasma generation may be carried out within the chamber containing the substrates (FIG. 6). A DC or a radio frequency potential is generally applied to the substrates during the deposition process. No external substrate heating is required. The substrate holder may be designed specifically to hold parts of different shapes such as cylinders, as would be apparent to one skilled in the field.

Useful variations of the above described methods for deposition of DLN films include, the use of sputtered silicon and oxygen gas as precursors for the Si and $O_2$, the use of sputtered carbon and hydrogen or hydrocarbon gas used as carbon and hydrogen precursors, or any combination thereof.

Figure 5:
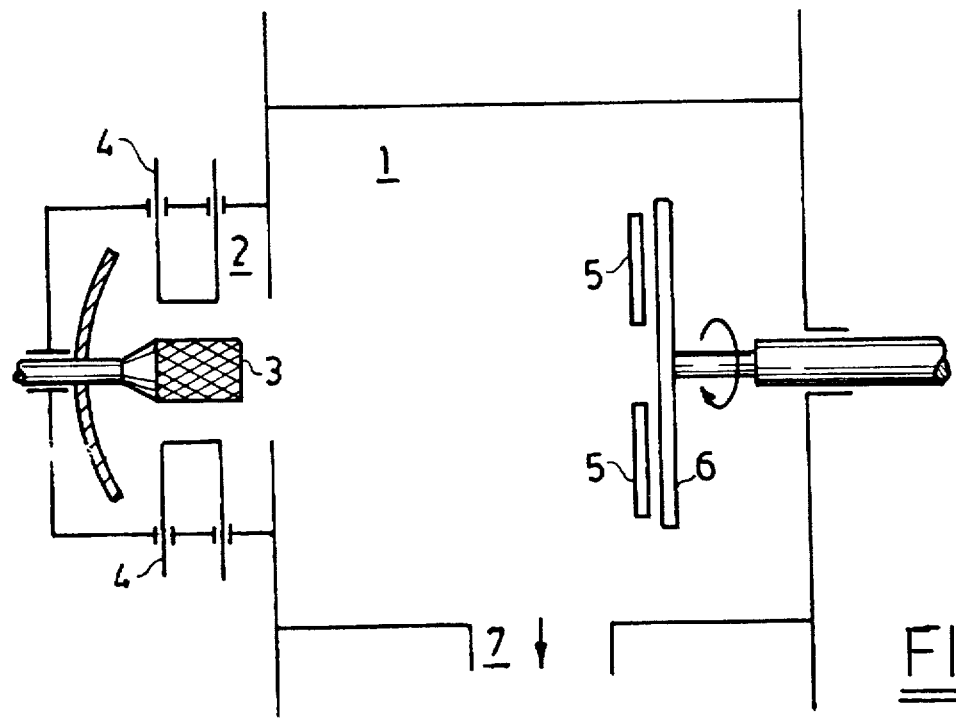
FIG. 5 is a cross section view of the deposition chamber for the deposition of DLNs using a reflecting electrode.

For deposition on non-conducting substrates, such as plastic, a method whereby a flow of neutral radicals is reflected from a high voltage target and directed to the substrate as shown schematically in FIG. 5. The process employs depositions similarly to those shown in FIG. 4, except that a reflecting electrode is used to generate a neutral beam. This process eliminates surface damage of the substrate resulting from charged and/or fast particles impinging on the substrate during growth.

A preferred method for depositing ultra-thin dielectric DLN films comprises ion bombardment (e.g. $Ar^+$ or $K^+$ with energy in the range of from about 30 to about 150 eV) through a vacuum chamber which has been backfilled by siloxane vapor (about $3 \times 10^{-4}$ torr). This results in a self-stabilized growth of a nanocomposite film, with the maximum thickness controlled by the maximum tunneling distance for the relaxation of the charge of the absorbed radicals.

Extremely uniform and nonporous ultra-thin dielectric films may be deposited according to the present invention. The thickness of the deposited DLN coating has no theoretical upper or lower limit. Existing technology and available equipment have allowed atomic-scale composite films and coating thicknesses typically in the range from about 1 µm to about 10 µm. According to this method, a film thickness in the range from about 6 to about 8 nm may be deposited, with a preferred deposited film thickness of from about 3 to about 5 nm.

Therefore, the above-described flexible coatings of the present invention may be deposited on the selected substrate in thicknesses ranging from a few nanometers to a few microns, preferably from about 20 nm to about 12 microns, depending only on the desired application of the coated substrate. The deposition may be tailored to meet the properties required for a particular application. The random interpenetrating of the two- or three-network DLNs guarantee uniform strength of the structures in all directions. The structures are free of micropores even at thicknesses of 80 Angstroms (8 nm). The DLNs are therefore extremely stable and possess unique combinations of chemical, mechanical, electronic, and superconducting properties.

The following examples serve only to further illustrate aspects of the present invention and should not be construed as limiting the invention.

EXAMPLE 1

Deposition of DLC, DLN and Me-DLN Coatings

DLC, DLN and Me-DLN coatings were prepared and deposited to compare the performance of the following thin films relative to the protection of plasma devices. Films were prepared on silicon substrates for preliminary property evaluations. The aluminum nitride targets used to prepare AlN-DLN coatings were prepared by hot pressing aluminum nitride powder A-100 produced by ART (Buffalo, N.Y.). Hot pressed boron nitride target plates were obtained from Advanced Ceramics Corp. (Ohio). Both targets were polished on one side. A polished beryllium target was procured from DFD Solid State Labs (NY). Magnetron sputtering of these targets was used to create the dopant-containing beams for Me-DLN films. DLN films were deposited using three different methods for performance comparisons with DLN and Me-DLN coatings. The different methods were used to ensure that results were not biased by the DLC deposition method. Seventeen samples of DLC coatings, and 27 samples of DLN, tungsten (W)-DLN, and beryllium (Be)-DLN were prepared and tested for ablation resistance under several conditions, including etching by atomic hydrogen containing arc-discharge, DC $Ar^+$ plasma, and laser ablation.

EXAMPLES 2–3

Flashover Testing

Flashover characteristics are an important consideration for coated insulators. It was determined during testing that dielectric breakdown strength was not necessarily a direct indicator of flashover behavior. Therefore, flashover measurements were carried out using two different methods on DLN deposited on sitall and HDPE (high density polyethylene) substrates. The effect of pressure was also considered. Overall, high flashover hold-off strengths were observed.

EXAMPLE 2

Measurements on Flat Sitall Substrates

Measurements were carried out using two separate experimental setups. In the first setup, 1 micron thick films of polymer-like film with the same composition as DLN were deposited 1) at the normal deposition conditions (1 kV), 2) in a 'soft mode' (0.3 kV), and also at 3) 0 kV. The substrate in each case was sitall, a microcrystalline ceramic material (HDPE was used for additional testing as described below). The width of the polyethylene spacer between the steel electrode bars was 0.09 mm, and it was raised above the film surface by approximately 0.1 mm. The length of each electrode was 42 mm. At an applied voltage of 1000V, for 10 minutes, no flashover was observed in the first two types of films. This is equivalent to a flashover resistance of over 110 kV/cm. For the film prepared according to 3) above, flashover was observed at 955+/−20 V (106 kV/cm).

EXAMPLE 3

Measurements on HDPE Substrates

Flashover measurements were carried out on HDPE substrates using the apparatus shown above. Since the available equipment was limited to a voltage of 1000V, the thickness of the spacers between the electrodes was reduced from 90μ to 17+/−0.5μ. Capacitor paper was used as the spacer. The DLN film was approximately 0.3μ thick. The length of the electrodes was 5 cm. The test was carried out in open air, with no extraordinary precautions taken to clean the surface. Then electrodes were pressed together firmly with the capacitor paper therebetween. Only the thickness of the capacitor paper was known. The exact distance between the electrodes was not directly measured. Voltage was increased in a controlled manner, and the current was measured across the electrodes. The current measurement device could measure to 0.1 microAmps. A current of 100–200 microAmps was observed above 500 V, and grew linearly with voltage. This rise was linear with voltage so long as there was no flashover. As the current approached 1 milliAmp, flashover became imminent. Visual observation occurred, current across the electrodes jumped sharply to 20–30 milliAmps.

EXAMPLE 4

Dielectric Strength Testing

DLN films grown on silicon substrates of p-type (boron-doped) and n-type (phosphorous-doped) were investigated. To assess the effect of high temperature annealing, certain films were subjected to 450° C. for 2 hr. in vacuum. Three approaches were used for creating a contact with DLN:

1) Metal Point Clamp (Contact area 10–20 mm$^2$]
2) Silver paste (Contact area 10–20 mm$^2$] ("Silver bond type 50", Transenc Co., Inc., NJ)
3) Pt films deposited on DLN by ion sputtering in the DLN deposition vacuum chamber, using masks.

The Pt contacts had a round shape with a diameter of 0.15 inches. Insulation between Pt contact spots was checked, and no current was observed up to 1 kV. Thee distance between these contacts was 1 mm. Thus no flashover was observed at a stress of 10$^4$ V/cm.

EXAMPLE 5

Plasma Ablation Testing

DLC films were deposited using three different methods for performance comparisons with DLN and Me-DLN coatings. Three different methods were used to ensure that results were not biased by the DLC deposition method. Seventeen samples of DLC coatings and 27 samples of DLN, W-DLN (tungsten) and Be-DLN (beryllium) were prepared and tested for ablation under several conditions, including etching by atomic hydrogen containing arc discharge, DC Ar$^+$ plasma, and laser ablation. Samples were exposed to an arc-discharge plasma from a mixture of methane and hydrogen. The gas pressure was 100 torr. The flow rate of hydrogen was 83 sccm$^{10}$ and the CH$_4$ content was 2.5–4 vol %. The substrate temperature measured by an optical pyrometer was 1000° C. The distance between the cathode and the substrate, used as an anode, was 15 mm. The cathode was made from TaC. The arc-discharge current was 1.5 Angstroms and the discharge area on the sample was 1 cm$^2$.

EXAMPLE 6

Laser Ablation

A KrF excimer laser was used to deliver 20 pulses of nanoosecond duration at a wavelength of 248 nm and a fluence of approximately 900 mJ/cm$^2$. The setup used produced uniform illumination of the film surface over a spot with diameter d=300μ. The light-induced changes in the optical properties of the films were monitored by measuring the reflectivity and transmittance of the modifying KrF laser radiation through the films and of He—Ne and He—Cd probe lasers. The probe light was detected and fed to amplifier and storage oscilloscope. The probe was positioned on the damaged spot and focused to a diameter of d=10μ, which was much smaller than the diameter of the zone affected by the excimer laser. The sample was mounted on a translation stage and moved perpendicular to the probe laser so that the reflectance was measured over the entire damage area. In general all three kinds of DLC were destroyed within 5 minutes, whereas the DLN coatings survived for over 1 hour with no changes in film structure.

EXAMPLE 7

Thermal Stability

The temperature stability of DLN coatings was deposited in a manner similar to that described in Example 1 was characterized by exposing sample substrates to elevated temperatures, followed by FTIR spectroscopy to evaluate any structural changes. No visible degradation was observed after exposure to elevated temperature for extended periods of time. No structural changes were observed as indicated by FTIR.

EXAMPLE 8

Effects of Ion and Electron Beam Exposure

Auger spectra of natural diamond, DLC, graphite and flame-synthesized diamond were collected for comparison with the evolution of Auger features for DLN irradiated with ion and electron beams. Auger spectra for DLN during continuous ion beam exposure were compared with the typical features for diamond, DLC, and graphite as described below. DLN and Me-DLN were stable under ion-beam irradiation.

Many other modifications and variations of the present invention are possible to the skilled practitioner in the field in light of the teachings herein. It is therefore understood that, within the scope of the claims, the present invention can be practiced other than as herein specifically described.

We claim:

1. An electrically tunable coating having a predetermined resistivity formed from interpenetrating networks, comprising a first network of bonded carbon in a diamond-like carbon network stabilized by hydrogen, a second silicon network stabilized by oxygen and, optionally, additional networks made from dopant elements, or dopant compounds containing elements from groups 1–7b and 8 of the periodic table.

2. The coating according to claim 1 wherein the carbon content is greater than about 40 atomic % of the coating, the hydrogen content is from about 1 atomic % up to about 40 atomic % of the carbon, and the sum of the silicon, oxygen and dopants together is greater than about 2 atomic % of the coating.

3. The coating according to claim 1 wherein the carbon, hydrogen, silicon and oxygen are obtained from the decomposition of an organosiloxane having from about 1 to about 10 silicon atoms.

4. The coating according to claim 3 wherein the organosiloxane is polyphenylmethylsiloxane.

5. The coating according to claim 1 wherein the carbon content is from about 40 wt. % to about 98 wt. %.

6. The coating according to claim 1 wherein the carbon content is from about 50 wt. % to about 98 wt. %.

7. The coating according to claim 1 wherein the carbon to silicon weight ratio is from about 2:1 to about 8:1.

8. The coating according to claim 1 wherein the silicon to oxygen weight ratio is from about 0.5:1 to about 3:1.

9. The coating according to claim 1 wherein the coating is deposited on a non-metal substrate.

10. The coating according to claim 1 wherein the dopant elements are selected from the group consisting of B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag and Au.

11. The coating according to claim 1 wherein the coating is a dielectric coating.

12. The coating according to claim 1 wherein the coating is a conductive coating.

13. The coating according to claim 1 wherein the coating has a surface resistivity value of from about $10^{-4}$ Ohm-cm to about $10^{15}$ Ohm-cm.

14. An anti-electrostatic coating formed from the coating of claim 1.

15. An ultracapacitor having multiple layers, one or more of the layers formed from the coating of claim 1.

16. An electrically tunable material with selectively modified resistivity made from a substrate and an electrically tunable coating, said coating made from a class of diamond-like solid state materials formed from interpenetrating networks, comprising a first network of bonded carbon in a diamond-like carbon network stabilized by hydrogen, a second silicon network stabilized by oxygen and, optionally, additional networks made from dopant elements, or dopant compounds containing elements from groups 1–7b and 8 of the periodic table.

17. The material according to claim 16 wherein the carbon content is greater than about 40 atomic % of the coating, the hydrogen content is from about 1 atomic % up to about 40 atomic % of the carbon, and the sum of the silicon, oxygen and dopants together is greater than about 2 atomic % of the coating.

18. The material according to claim 16 wherein the carbon, hydrogen, silicon and oxygen are obtained from the decomposition of an organosiloxane having from about 1 to about 10 silicon atoms.

19. The material according to claim 18 wherein the organosiloxane is polyphenylmethylsiloxane.

20. The material according to claim 16 wherein the carbon to silicon weight ratio is from about 2:1 to about 8:1.

21. The material according to claim 16 wherein the silicon to oxygen weight ration is from about 0.5:1 to about 3:1.

22. The material according to claim 16 wherein the dopant elements are selected from the group consisting of B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag and Au.

23. The material according to claim 16 wherein the coating is a dielectric coating.

24. The material according to claim 16 wherein the coating is a conductive coating.

25. The material according to claim 16 wherein the coating has a surface resistivity value of from about $10^{-4}$ Ohm-cm to about $10^{15}$ Ohm-cm.

26. An anti-electrostatic material formed from the material of claim 16.

27. An ultracapacitor having multiple layers, one or more of the layer formed from the material of claim 2.

28. A rectifying contact for Schottky barriers formed from the material of claim 16.

29. A thermal resistor for inkjet printers formed from the material of claim 16.

* * * * *